United States Patent
Li et al.

(10) Patent No.: US 8,669,046 B2
(45) Date of Patent: Mar. 11, 2014

(54) REAGENTS AND METHODS FOR DETECTING INFLUENZA VIRUS PROTEINS

(76) Inventors: Xuguang (Sean) Li, Ontario (CA); Runtao He, Manitoba (CA); Gary Van Domselaar, Manitoba (CA)

( * ) Notice: Subject to any disclaimer, the term of this patent is extended or adjusted under 35 U.S.C. 154(b) by 129 days.

(21) Appl. No.: 12/920,838

(22) PCT Filed: Mar. 10, 2009

(86) PCT No.: PCT/CA2009/000283
§ 371 (c)(1),
(2), (4) Date: Nov. 22, 2010

(87) PCT Pub. No.: WO2009/111865
PCT Pub. Date: Sep. 17, 2009

(65) Prior Publication Data
US 2011/0059472 A1 Mar. 10, 2011

Related U.S. Application Data

(60) Provisional application No. 61/064,570, filed on Mar. 12, 2008.

(51) Int. Cl.
| | |
|---|---|
| C07K 16/10 | (2006.01) |
| G01N 33/569 | (2006.01) |
| C07K 7/08 | (2006.01) |
| C07K 17/06 | (2006.01) |
| C12Q 1/70 | (2006.01) |
| A61K 39/145 | (2006.01) |

(52) U.S. Cl.
USPC ............ 435/5; 435/7.1; 530/327; 530/387.9; 530/389.4; 530/403; 530/405; 530/413; 424/186.1

(58) Field of Classification Search
None
See application file for complete search history.

(56) References Cited

U.S. PATENT DOCUMENTS

| 2011/0046354 A1* | 2/2011 | Sinha et al. | 530/387.3 |
| 2012/0070455 A1* | 3/2012 | He et al. | 424/186.1 |
| 2012/0141519 A1* | 6/2012 | Li et al. | 424/186.1 |

FOREIGN PATENT DOCUMENTS

WO    WO 2004/080403    *    9/2004

OTHER PUBLICATIONS

Horvath et al., Immunology Letters 1998 vol. 60, pp. 127-136.*
Horvath A et al: "Hemagglutinin-Based Multipeptide Construct Elicitis Enhanced Protective Immune Response in Mice Against Influenza A Virus Infection", Immunology Letters, elsevier BV, NL, vol. 60, No. 2/03, Feb. 1, 1998, pp. 127-136.
Bianchi Elisabetta et al: "Universal Influenza B Vaccine Based on the Maturational Cleavage Site of the Hemagglutinin Precursor", Journal of Virology, The American Society for Microbiology, US, vol. 79, No. 12, Jun. 1, 2005, pp. 7380-7388.
Nestorowicz A et al: "Antibodies Elicited by Influenza Virus Hemagglutinin Fail to bind to Synthetic Peptides Representing Putative Antigenic sites.", Molecular Immunology Feb. 1985, vol. 22, No. 2, Feb. 1985, pp. 145-154.
Gerhard W et al: "Prospects for Universal Influenza Virus Vaccine", Emerging Infectious Diseases, EID, Atlanta, GA, US, vol. 12, No. 4, Apr. 1, 2006, pp. 569-574.
Chun S et al: "Universal Antibodies and their Applications to the Quantitative Determination of Virtually all Subtypes of the Influenza A Viral Hemagglutinins", Vaccine, Elsevier Ltd, GB, vol. 26, No. 48, Nov. 11, 2008, pp. 6068-6076.
Scott D et al: "Immunogenicity of Boitinylated Hapten-Avidin Complexes", Molecular Immunology, Pergamon, GB, vol. 21, No. 11, Nov. 1, 1984, pp. 1055-1060.

* cited by examiner

*Primary Examiner* — Mary E Mosher
*Assistant Examiner* — Myron Hill
(74) *Attorney, Agent, or Firm* — Michael R. Williams; Ade & Company Inc.

(57) ABSTRACT

Antibodies that specifically bind to a peptide having an amino acid sequence as found at the N-terminus of the HA2 fusion peptide of the influenza A virus may be raised by inoculating a mammal with a conjugate of the peptide. In one embodiment, the conjugate comprises the peptide linked to a spacer (e.g. 6-aminocaproic acid) and a carrier protein (e.g. KLH). The antibodies may be used as a universal reagent for detecting HA proteins of influenza viruses. The antibodies are useful as versatile reagents for laboratory research and vaccine potency determination, especially in the event of pandemic influenza outbreaks.

19 Claims, 5 Drawing Sheets

Sequence Homology of N-terminus of Fusion Peptide
of Human and Avian Influenza Virus Strains

| Position | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Amino acid | G | L/I | F | G | A | I | A | G | G | I | E | G/N | G | W |
| % homology | 100% | 66.898% | 99.85% | 99.7% | 99.95% | 99.9% | 99.9% | 99.9% | 100% | 99.9% | 99.95% | 54.62% | 100% | 100% | amino acid and amino acid position (HA2)

Measurement of the Concentration of HA Antigens
in Solution in Competitive ELISA concentration of antigen in solution (μg/ml)

OD values (at 450 nm)

Fig. 4

Detection of H5N1 Recombinant Hemagglutinin
Using the Universal Antibodies as Primary Antibodies P1    P2    Pt1    Pt2    Cl

Fig. 5

REAGENTS AND METHODS FOR DETECTING INFLUENZA VIRUS PROTEINS

CROSS-REFERENCE TO RELATED APPLICATIONS

This application claims the benefit of U.S. Provisional Patent Application U.S. Ser. No. 61/064,570 filed on Mar. 12, 2008, the entire contents of which is herein incorporated by reference.

FIELD OF THE INVENTION

The present invention relates to reagents and methods for detecting influenza virus proteins, in particular hemagglutinins (HA). In particular, the present invention relates to peptide conjugates, antibodies, and use of antibodies for detecting hemagglutinins in a sample, especially for verifying potency of influenza vaccines.

BACKGROUND OF THE INVENTION

Influenza can infect as much as 5-15% of the world population, resulting in 3-5 million cases of severe illness and up to 500,000 deaths each year. In the U.S. alone, flu epidemics lead to approximately 300,000 influenza-related hospital admissions and 36,000 influenza-related deaths annually in addition to an estimated cost of $12 billion per year (Poland 2001; Simonsen et al. 2007, PMID: 17897608). Current seasonal influenza vaccines are produced with strains recommended by the World Health Organization about 9-12 months ahead of the targeted season (Carrat et al. 2007). The vaccines typically contain two type A influenza strains and one type B, which are predicted to be the most likely strains to cause the upcoming flu epidemic.

However, there are inherent disadvantages associated with the preparation of conventional influenza vaccines such as the uncertainty of the actual circulating strain, the need for annual updating of the manufacturing process and preparation of reagents for vaccine lot release. Furthermore, mismatches between the strains selected for vaccine preparation and the circulating viruses were found to be responsible for much reduced efficacy of the seasonal influenza vaccines (Bridges et al. 2000; De Filette et al. 2005). Clearly, the drawbacks associated with traditional vaccine preparation would be drastically exacerbated in the event of an outbreak of pandemic influenza, given a perceivably much shortened timeframe available for the production of prophylactic vaccines for global needs. All these problems concerning the influenza vaccines are largely due to one single biological property of the influenza virus itself, i.e. the constant mutations of the virus surface proteins hemagglutinin (HA) and neuraminidase (NA). Currently HA is used as the "marker" being tested for vaccine potency (Wood et al. 1999).

Currently, influenza A viruses representing 16 HA and 9 NA subtypes have been detected in wild birds and poultry throughout the world (Zambon 1999; Treanor 2004; Fouchier 2005). Frequent antigenic drifting or shifting of HA and NA prompted numerous exploratory investigations of vaccines that are intended to induce host immune responses against viral proteins that are less subjected to antigenic fluctuations. Of these conserved antigenic determinants, the nucleoproteins (NP) and Matrix (M) have been shown to induce protective immunity against diverse strains of the viruses (Frace et al. 1999; Epstein et al. 2002; de Filette 2005; Mozdzanowska et al. 2003; Fan et al. 2004). Furthermore, it was suggested that cell-mediated immune response rather than humeral immune responses protect the animals immunized with NP-based vaccines while antibody-mediated protections against lethal challenges of various subtypes of influenza virus were reported with the use of M2-based vaccines (Neirynck et al. 1999; de Filette et at 2005; Mozdzanowska et al. 2003). None of these universal vaccines appears to prevent viral infection in animal studies although prevention of clinical diseases was found to be promising (Gerhard et al. 2006).

Given the importance of neutralizing antibodies against HA in preventing influenza infection, the conserved regions in the HA proteins have also received great attention in recent years. The HA1/HA2-joint region has been found to be the most broadly conserved, with the HA2 N-terminal 11 amino acids being conserved among all influenza A subtypes (Horvath et al. 1998; Bianchi et al. 2005; Gerhard et al. 2005). Several groups have reported generation of antibodies against the HA1/HA2 joint region with the use of branched peptides or peptide-carrier conjugate (Nestorowicz et al. 1985; Schoofs 1988; Horvath et al. 1998; Bianchi et al. 2005). Yet, attempts to generate antibodies against the even more universally conserved N-terminus of the HA2 (the fusion peptide) have not been that successful (Jackson, et al. 1991; Nestorowicz et al. 1985; Schoofs 1988; Horvath et al. 1998; Bianchi et al. 2005).

There remains a need in the art for reagents that may be universally used to detect influenza viruses or proteins therein, especially hemagglutinin (HA) proteins.

SUMMARY OF THE INVENTION

It has now been surprisingly found that antibodies that specifically bind to a peptide having an amino acid sequence as found at the N-terminus of the HA2 fusion peptide of the influenza A virus may be raised, and that such antibodies may be used as universal reagents for detecting HA proteins of influenza viruses. The antibodies are useful as versatile reagents for laboratory research and vaccine potency determination, especially in the event of pandemic influenza outbreaks.

In accordance with a first aspect of the present invention, there is provided a conjugate comprising: a conserved influenza virus peptide having an amino acid sequence as found at N-terminus of an HA2 fusion peptide of an influenza A virus; a spacer molecule linked to the conserved influenza virus peptide; and a carrier protein linked to the spacer molecule.

In accordance with a second aspect of the present invention, there is provided an antibody that binds specifically to a peptide having an amino acid sequence at N-terminus of an HA2 fusion peptide of an influenza A virus.

In accordance with a third aspect of the present invention, there is provided a method of detecting influenza hemagglutinin proteins in a target sample comprising: contacting an antibody of the present invention with the target sample; and, determining whether the antibody binds to the sample.

In accordance with a fourth aspect of the present invention, there is provided a method for determining potency of an influenza vaccine comprising: contacting an antibody of the present invention with a vaccine; and, determining whether the antibody binds to an element in the vaccine.

In accordance with a fifth aspect of the present invention, there is provided a process for preparing an antibody comprising inoculating a mammal with a conjugate of the present invention.

In accordance with a sixth aspect of the invention, there is provided a modified peptide comprising: a conserved influenza virus peptide having an amino acid sequence as found at N-terminus of an HA2 fusion peptide of an influenza A virus; and, a spacer molecule linked to the conserved influenza virus peptide.

The amino acid sequence of the peptide at the N-terminus of the HA2 fusion peptide of the influenza A virus preferably comprises 14 amino acids. Preferably, greater than 90% of the amino acids are neutral and/or non-polar. The sequence preferably comprises SEQ ID NO: 6, for example SEQ ID NO: 1, SEQ ID NO: 2, SEQ ID NO: 3 or SEQ ID NO: 4.

Any suitable spacer molecule or combination of spacer molecules may be used. Spacer molecules include, for example, amino acids, peptides, phosphoramidite, ε-aminohexanoic acid and 6-aminocaproic acid. More than one spacer molecule may be used, but care must be taken to avoid solubility problems. The spacer molecule preferably comprises 6-aminocaproic acid.

The carrier protein may be any suitable carrier, for example keyhole limpet hemocyanin (KLH), bovine serum albumin (BSA), rabbit serum albumin (RSA), ovalbumin (OVA), thyroglobulin (THY) and human gamma globulin (HGG). KLH is preferred.

The conserved influenza virus peptide modified with the spacer may be further modified with an appropriate linker. The linker is preferably an amino acid or a peptide having 2-10 amino acids. The linker may facilitate linking the modified peptide to the carrier protein. Generally, the linker links the spacer of the modified peptide to the carrier protein. The linker may be chosen to provide further useful properties, for example to facilitate dissolution of the modified peptide in aqueous solution. A tripeptide linker, particularly KKC, is preferred.

To raise antibodies against the conserved influenza virus peptide, a mammal may be inoculated with a conjugate of the present invention. Some examples of mammals are rabbit, mouse, rat, hamster, human, deer. The antibodies so raised are preferably purified for further use.

The antibodies may be used for detecting and/or quantifying the presence of influenza hemagglutinin (HA) proteins in a sample. The antibodies are universal, permitting detection and/or quantification of HA proteins from many different influenza virus strains, including influenza A and B strains. The universality of the antibodies makes them excellent reagents for determining the potency of influenza vaccines. The antibodies may also be used in earlier stages of seasonal influenza vaccine manufacturing, for example, to estimate presence and/or potency of influenza HA proteins prior to availability of the subtype specific antisera. The antibodies also permit manufacturing of seasonal influenza vaccine at least 2-3 months ahead of the current schedule, thus greatly facilitating prompt production of the seasonal influenza vaccines and timely release of the vaccines prior to an upcoming flu season.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which:

FIG. 1 depicts sequence homology of influenza A virus. A total of 3200 sequences from public domains (the NCBI flu resource) were retrieved separately for each subtype. The combined human and avian influenza HA sequences with identical sequences were removed. A separate multiple alignment for each subtype was performed, followed by the extraction of the target region from the full-gene alignment. The Shannon entropy for each position of amino acid of the identified consensus sequences was calculated to determine the degree of variation. There were 2012 amino acids from the combined human and avian strains. Only two positions have noticeable substitutions: position 2 from L to I (neutral and non-polar to neutral and non-polar) (665/2012-33.05%, or F) and position 12 from G to N (neutral and non-polar to neutral and polar) (912/2012=45.32%).

FIG. 2 depicts generation of antibodies against fusion peptides and binding of antibodies.

FIG. 3A: Allantoic fluids of 13 subtypes of influenza viruses propagated in embryonated eggs were fractionated in SDS-PAGE, followed by detection of the HA proteins using the Uni-1 antibodies (upper gel panel). Rabbit polyclonal anti-NP proteins of influenza viruses were used as another control (lower gel panel). Note that the different mobilities of the HA proteins are due to the difference in size or processing stages of the various subtypes of viruses. "Ctr" denotes the negative control (allantoic fluid from un-infected eggs).

The antigens were denatured in 8 M urea (for detail refer to *Materials and Methods* below). In brief, the urea-denatured antigen in 4 M urea/PBS was coated in 96-well plate at 4° C. for overnight. The following morning, the competing antigens at serially-diluted concentrations were mixed with the universal antibodies, and transferred directly to the 96-well plate which had been coated with the antigens. FIG. 4 shows that the concentration of the antigen in solution (competing antigen) plotted on x axis (μg/ml), is inversely proportional to the optical density plotted on y axis (OD values at 450 nm).

FIG. 5 depicts detection of HA proteins directly absorbed on nitrocellulose filter (Dot Blot). The procedure is the same except that H5N1 recombinant HA protein antigen (0.5 μg in 10 μL) were directly applied to the nitrocellulose. There is no need to denature the HA proteins. P1 and P2 represent pre-bleed sera from rabbit #1 and rabbit #2 respectively. Pt1 and Pt2 represent antisera obtained after 4 boosts for rabbit #1 and rabbit #2 respectively. CI denotes negative control with no primary antibodies. Film was exposed for 1 minute.

DESCRIPTION OF PREFERRED EMBODIMENTS

Antigenic drifting and shifting of the influenza A viruses have presented to the scientific community a daunting challenge in terms of epidemiological monitoring, vaccine development and quality control. We have now generated and characterized antibodies against the most conserved region (fusion peptide) in the hemagglutinins of influenza A viruses. Bioinformatics analyses of all available hemagglutinin (HA) sequences from public domain revealed a stretch of 14 amino acids comprised of G [L/I] FGAIAGFIE[G/N]GW (SEQ ID NO: 6), which are neutral and/or non-polar except the glutamic acid (E) which is acidic and polar. This region, starting at the N-terminus of HA2, was found to be universally present in all viral strains with minor substitutions.

To overcome the weak immunogenicity and insolubility of the peptide, we linked the peptide to 6-aminocaproic acid, followed by the addition of a charged tripeptide (KKC) before its conjugation to the carrier protein KLH (keyhole limpet hemocyanin). We found rabbits generated specific antibodies with equal binding efficiency for four peptides which represent the variations in the fusion peptide epitope. The 6-aminocaproic acid spacer was important in inducing antibodies against the fusion peptides.

In solution, the epitope was partially shielded from binding to the antibodies but exposed following treatments with urea. Moreover, the antibodies still retain full antigen-binding abilities in 4 M urea, a condition necessary for the quantitative determination of HA amounts in solution. The specificity of the antibodies was assayed in Western Blot using a wide range of subtypes of influenza A viruses (H1-H13) in crude allantoic fluid preparations. The antibodies were found to bind all HAs with similar intensities while demonstrate no cross-relativities to egg proteins. Moreover, versatility of the antibodies was demonstrated in a variety of immunoassays, making them universal reagents for quantitative analyses of seasonal and candidate pandemic influenza vaccines as well as useful research tools in laboratory settings. To our knowledge, this is the first report on the generation of universal antibodies exclusively against the fusion peptide region.

Materials and Methods:

Preparation of Peptides and their Conjugates for Immunization

Bioinformatics approach was employed to locate the presence of the universally conserved region in the HAs. Sequences from public domains (the NCBI flu resource) were retrieved separately for each subtype. The combined human and avian influenza HA sequences with identical sequences were removed. Next, a separate multiple alignment for each subtype was performed, followed by the extraction of the target region from the full-gene alignment. The Shannon entropy for each position of amino acid of the identified consensus sequences was then calculated to determine the degree of variation. Four peptides were selected to ensure a good coverage of the fusion peptide region. These peptides, GLFGAIAGFIEGGW (SEQ ID NO: 1) (Uni-1); GIFGAIAGFIEGGW (SEQ ID NO: 2) (Uni-2); GLFGAIAGFIENGW (SEQ ID NO: 3) (Uni-3); and GIFGAIAGFIENGW (SEQ ID NO: 4) (Uni-4), were then modified and conjugated in a procedure described previously with minor modification (Wu et al. 1993; Das Sarma et al. 2005). In brief, the peptides were first linked to 6-aminocaproic acid, followed by an addition of a tripeptide (KKC). The modified peptides were then conjugated to the carrier protein KLH using sulfosuccinimidyl-4-(N-maleimidomethyl)cyclohexane-1-carboxylate (Sulfo-SMCC) as cross-linking reagent and purified according to the manufacturer's instruction manual (Fisher Canada, Nepean, On.). Table 1 summarizes the peptides (Uni-1, Uni-2, Uni-3 and Uni-4) and conjugates thereof used for the generation and characterization of specific antibodies against the N-terminus of influenza viruses.

Table 1 depicts the four peptides (Uni-1 to Uni-4) located at the N-terminus of HA2 of influenza virus strains. The selection of these peptides was based on bioinformatics analyses of all available influenza HA sequences and represent the most conserved amino acid sequences in the fusion peptide region with minor variations. HA1-C is a control peptide VTGLRNIPSIQSR (SEQ ID NO: 5) located at the C-terminus of HA1. Acp denotes 6-aminocaproic acid, an effective spacer to link haptens (dinitrophenyl) to carrier proteins (Scott et al. 1984). KKC represent a tripeptide, which was used here to facilitate solubilization of the carrier-free peptides in aqueous solution for antigen-antibody interaction in ELISA. KLH designates keyhole limpet hemocyanin.

TABLE 1

| Designation of Peptide | Conjugate | Representative Virus Strains (NCBI Accession Number) |
|---|---|---|
| Uni-1 | GLFGAIAGFIEGGW-[Acp]-KKC-KLH | H1N1 (AAP34324) |
| Uni-2 | GIFGAIAGFIEGGW-[Acp]-KKC-KLH | H9N2 (EF154959.1) |
| Uni-3 | GLFGAIAGFIENGW-[Acp]-KKC-KLH | H7N7 (AB307735.1) |
| Uni-4 | GIFGAIAGFIENGW-[Acp]-KKC-KLH | H3N2 (EU100670.1) |
| HA1-C | VTGLRNIPSIQSR-[Acp]-KKC-KLH | H1N1 (CY026523.1) |

Viruses, Recombinant Proteins and Vaccines

Table 2 lists the viruses, recombinant hemagglutinins and human vaccines used in the characterization of the antibodies. The influenza virus strains listed are derived from the inventory at the National Institute for the Control of Pharmaceutical and Biological Products, Beijing. All the virus strains have been confirmed with reference sera according to internationally accepted criteria (Rohm et al. 1996; Fouchier 2005; World Health Organization 1980). The viruses were propagated in embryonated chicken eggs. The recombinant HAs were purchased from Proteins Sciences Corporation as described previously (Wang et al. 2006). The trivalent annual influenza vaccines (H1N1/H3N2/B) were generously provided by the National Institute for the Control of Pharmaceutical and Biological products, Beijing, China.

TABLE 2

| Subtype | Strains | Isolation Date |
|---|---|---|
| Influenza Virus | | |
| H1N1 | DK/ST/1734/03 | 2003 |
| H2N8/N4 | DK/ST/992/00 | 2000 |
| H3N3 | DK/ST/708/00 | 2000 |
| H4N6 | DK/SIBERIA/378/01 | 2001 |
| H6N1 | TEAL/HK/W312/97 | 1997 |
| H7 | DK/C/A47 | 1947 |
| H8N4 | TUEKEY/Ontario/6118/68 | 1968 |
| H9N2 | Qa/HK/G1/97 | 1997 |
| H10N4/N8 | DK/ST/1796/01 | 2001 |
| H11N1/N8 | DK/ST/834/01 | 2001 |
| H12N5 | DK/HK/838/80 | 1980 |
| H13N5 | Gull/MD/704/77 | 1977 |
| Recombinant Hemagglutinins | | |
| H1N1 | A/New Caledonia/20/99 | 1999 |
| H3N2 | A/Wisconsin/67/05 | 2005 |
| H5N1 | A/Vietnam/1203/2004 | 2004 |
| H7N7 | A/Netherlands/219/03 | 2003 |
| H9N2 | A/Hong Kong/1073/99 | 1999 |
| Human Vaccine | | |
| H1N1 | A/Solomon Islands/3/2006 | 2006 |
| H3N2 | A/Wisconsin/67/2005 | 2005 |
| Influenza B | B/Malaysia/2506/2004 | 2004 |
| H5N1 | A/Indonesia/5/05 | 2005 |

Production of Antibodies Against the Fusion Peptides of HAs

NZW rabbits were obtained from Jackson Laboratory. All animal experiments were conducted in accordance with the Institutional Guidelines and Protocols for Animal Experiments. The animals were immunized subcutaneously with various types of peptide-KLH conjugate mixed with freund complete adjuvant (FCA) at 200 µg per injection, and boosted every three weeks with the same doses of antigen in freund incomplete adjuvant. The antibodies were purified by using the peptides as ligands in affinity columns in a procedure described previously (Wu et al. 1993). In brief, the antisera were incubated with 5 mL of the peptide on a column for 10 min at room temperature, followed by washing the column at least 5 times with PBS and 0.1% Tween™-20. The antibodies were then eluted with acetate buffer (pH 2.0), followed by immediate addition of sodium hydroxide to bring the pH to 7.2 (Wu et al., 1993).

Immunoblotting

The specificities of the antibodies were determined in Western Blot using a procedure with minor modifications as described (Casley et al. 2007). In brief, allantoic fluids directly from eggs inoculated with viruses were fractionated on sodium dodecyl sulfate (SDS)-10% polyacrylamide gel, followed by transferring the samples to a nitrocellulose filter. The nitrocellulose filter was then blocked with 5% BSA/PBS at 37° C. for 1 hr. Following incubation of filters for 1 hr at 37° C. with rabbit antisera against HA peptides as described above, peroxidase-conjugated goat anti-rabbit immunoglobulin (Ig) G (Sigma, Oakville, Canada) was added for an additional incubation of 1 h at room temperature, followed by chemiluminescent detection (ECL, Amersham Pharmacia Biotech, Piscataway, N.J.). In some cases, dot blotting was used to determine antigen-antibody interaction. The procedure is essentially the same as Western Blot except that the antigens (10 µL) were directly spotted on the nitrocellulose filter.

ELISA

Indirect ELISA was performed in a procedure as described (Huang et al 2008). In brief, 4 µg/mL of HA protein or 1 µg/mL of peptides were coated onto 96-well plate (Nunc/VWR, Mississauga, On) at 4° C. overnight. The wells were then washed five times with PBS, 0.05% Tween™-20, followed by the addition of blocking buffer comprised of PBS, 0.05% Tween™-20 and 5% BSA. After incubation at 37° C. for 1 h, the blocking buffer was removed, followed by the addition of primary antibodies. The plates were incubated again at 37° C. for 1 h. Afterwards, secondary antibodies (peroxidase-conjugated goat anti-rabbit IgG, IgM or IgA) were added at concentrations recommended by the supplier (Cedarlane Labs). Following an additional incubation at 37° C. for 1 h, the plates were washed five times before o-phenylenediamine dihydrochloride (OPD) was added for colorimetric development. The cut-off was defined as mean of five negative samples (from pre-bleed control) plus two STD.

Competitive ELISA was performed as described below. The antigens were first denatured with 8 M in PBS urea for 20 min at room temperature, followed by mixing with equal volume of PBS to allow final concentration of antigen at 4 µg/mL in 4 M urea/PBS. The antigens were then used to coat the Nunc 96-well plate at 4° C. overnight. The next day, the antigens were denatured with 8 M urea/PBS for 20 min at room temperature, followed by mixing with 8,000× diluted antisera. The final concentration of urea in the antigen-antibody mixture is 4 M. The mixture was then transferred to the aforementioned 96-well ELISA plate which had been pre-coated with the antigens and subsequently blocked with 5% BSA/PBS. The plate was then incubated at 37° C. for 1 hr. The rest of the procedure was the same as that in ELISA.

Figure 1:
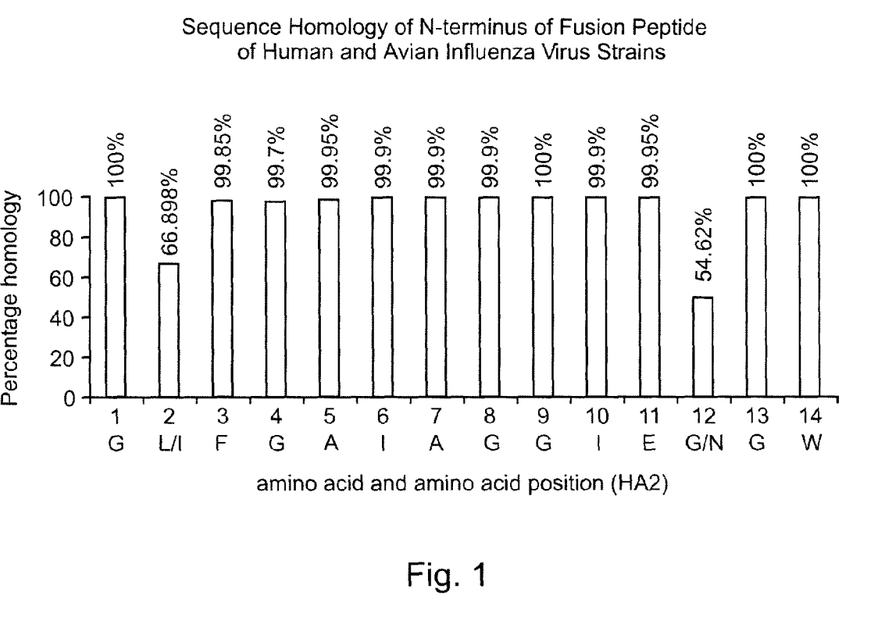

Results:

Selection of Peptides for the Generation of Antibodies Against Diverse Strains of Influenza Viruses Following a comprehensive analysis of the public database, the most conserved sequences were determined to be in the fusion peptide (the amino terminus of the HA2 polypeptide), largely agreeing with other investigators (Jackson et al. 1991; Horvath et al. 1998; Bianchi et al. 2005; Gerhard et al. 2006). However, it is of note that there are some minor variations as a result of bioinformatics analyses (see *Materials and Methods* above). Of the N-terminal 14 amino acids of the HA2, at position 2 a change from leucine (L) to isoleucine (I) with a frequency of approx. 33% was noted while at position 12 from glycine (G) to asparagines (N) at a rate of approx. 45% (FIG. 1). In light of these findings, four peptides were chosen to ensure a good coverage of all influenza strains as listed in Table 1. All four peptides were extremely hydrophobic, thus presenting daunting challenge to the subsequent peptide manipulations such as synthesis, purification, conjugation and epitope mapping in immunoassays.

Figure 2A:
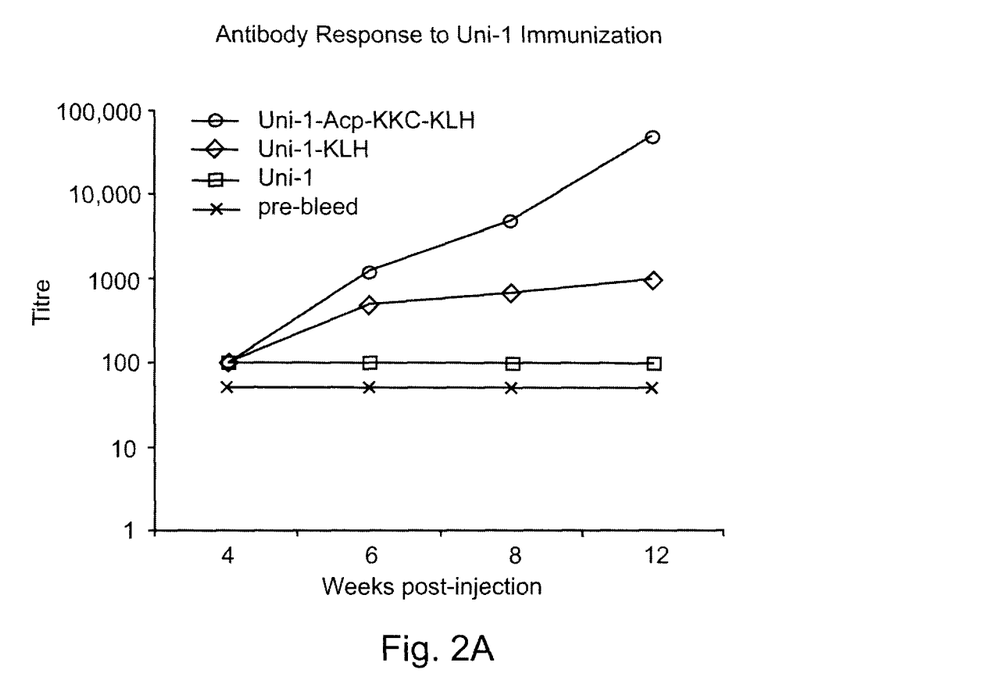
FIG. 2A depicts the antibody responses against the Uni-1 peptide following immunization with various forms of fusion peptides. In brief, modified Uni-1 conjugated to KLH (Uni-1-Acp-KKC-KLH), Uni-1 without 6-aminocaproic acid but conjugated to KLH (Uni-1-KKC-KLH), and unmodified and un-conjugated Uni-1 were injected into rabbits (2 each) subcutaneously and boosted every two week. Indirect ELISA with Uni-1-Acp-KKC-KLH as coating antigens was used to measure the titre of antibodies against the peptides.

One of the four peptides, Uni-1 (SEQ ID NO: 1) in Table 1, was used for peptide modification and conjugation while the other peptides were used for epitope mapping of the antibodies generated from immunization with Uni-1 conjugate. Towards this end, Uni-1 was first linked with a spacer (6-aminocaproic acid) to improve immunogenicity (Scott et al. 1984), followed by a tripeptide (KKC) to enable solubilization of the peptide and also provide the cysteine residue necessary for conjugation to the KLH carrier. The peptides or peptide-conjugates were injected into NZW rabbits, followed by boosting every two weeks. Significant antibody response was generated in NZW rabbits against the Uni-1-Acp-KKC-KLH conjugate. The antibodies generated were IgG antibodies. As shown in FIG. 2A, the presence of spacer (6-aminocaproic acid) between the influenza amino acid sequence (Uni-1) and the carrier (KLH) was found to be important in eliciting antibodies against the viral sequences in ELISA assay using Uni-1 peptide as coating antigens (FIG. 2A). As expected, Uni-1 without carrier KLH failed to elicit any antibody response.

Figure 2B:
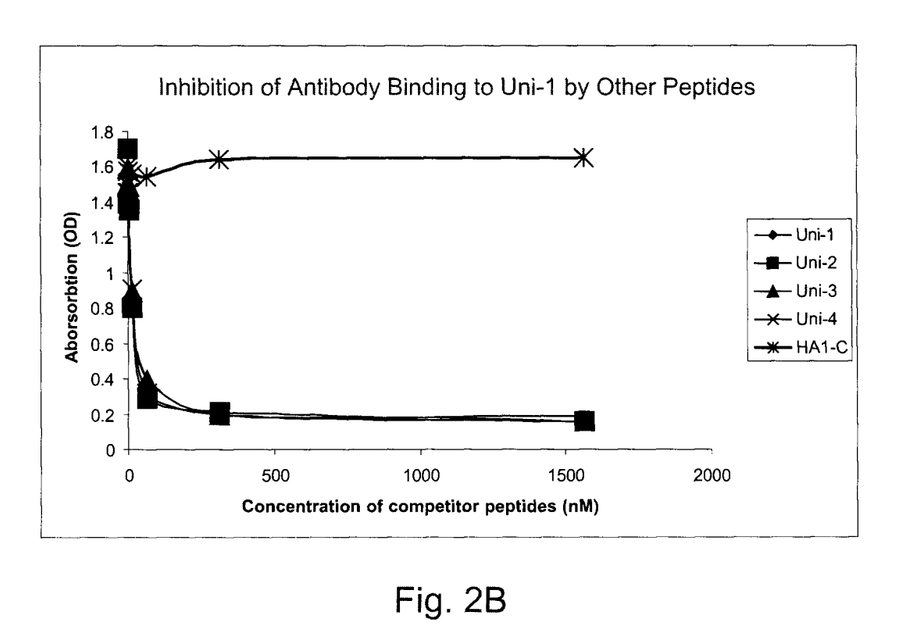
FIG. 2B shows that Uni-2, Uni-3 and Uni-4 peptides were able to compete with Uni-1 in binding to the antibodies. Briefly, Uni-1-Acp-KKC were coated in ELISA plates. The antibodies were then pre-incubated with Uni-2-Acp-KKC, Uni-3-Acp-KKC, Uni-4-Acp-KKC or HA1-C-Acp-KKC (control peptide) respectively, followed by transferring the mixtures to the ELISA plates which had been pre-coated with Uni-1-Acp-KKC. Anti-rabbit IgG conjugated-to HRP were then added to determine the residual antibodies in the mixture.
Figure 3A:
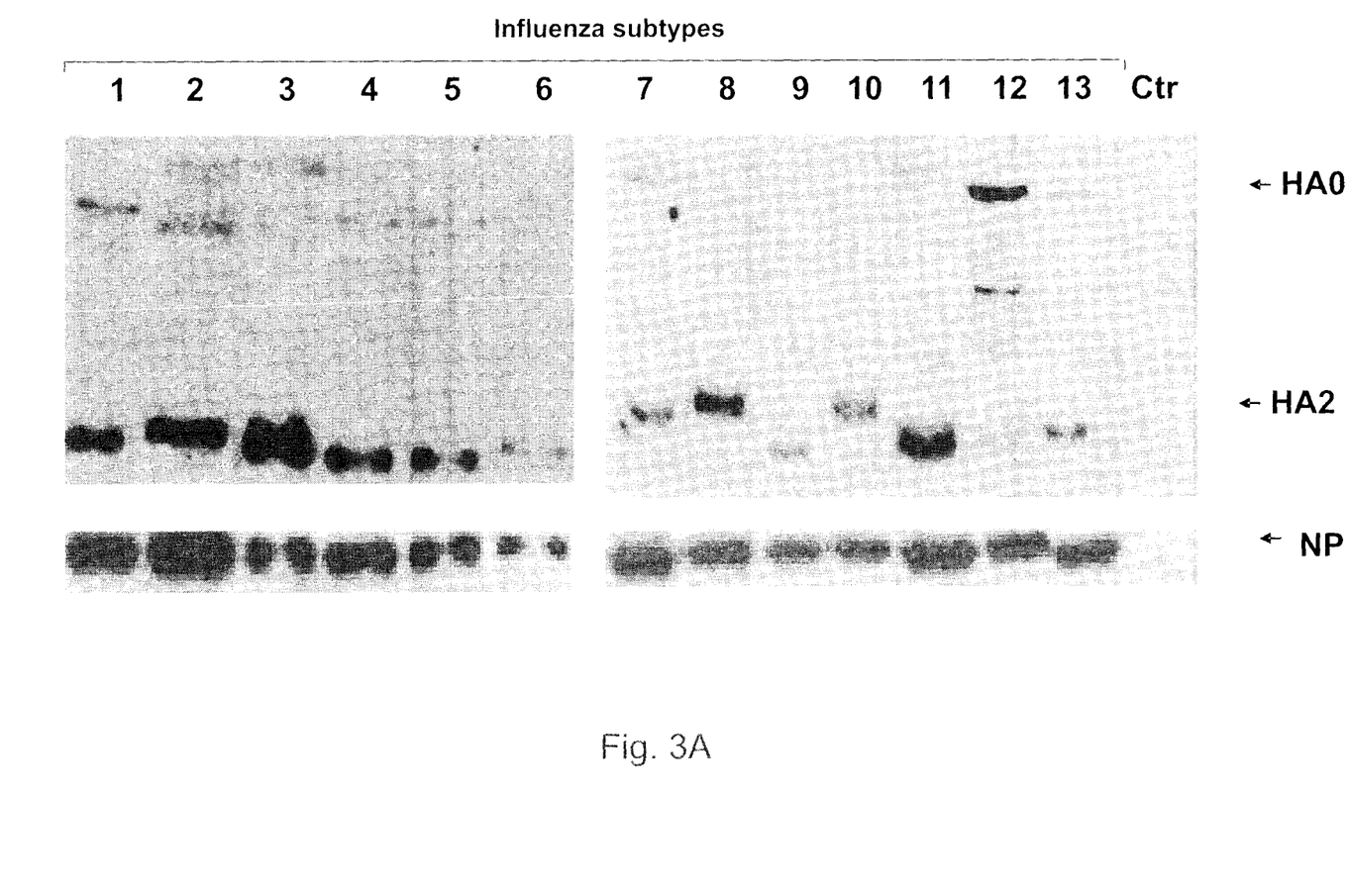
FIG. 3 depicts determination of binding specificity of antibodies against influenza virus in W.B.
Figure 3B:
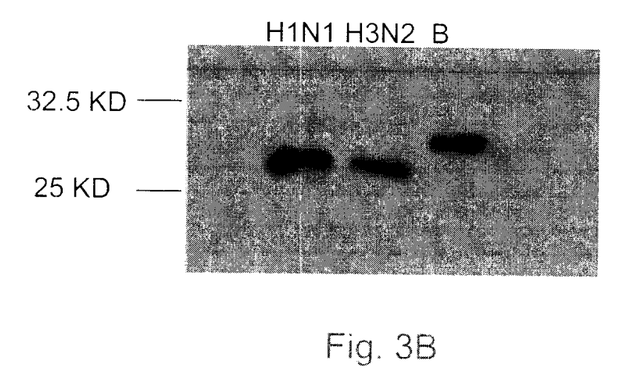
FIG. 3B: Detection of influenza HA proteins from purified viruses in human vaccine preparations.
Figure 3C:
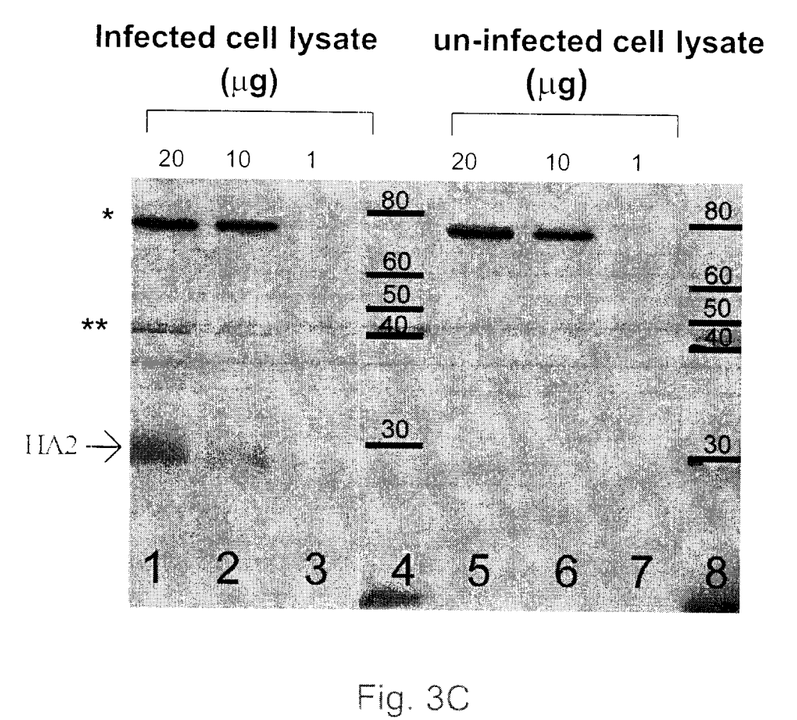
FIG. 3C: Detection of HA proteins in MDCK cells infected with influenza virus (H1N1, PR8). Lanes 1, 2 and 3 represent 20, 10 and 1 μg of cell lysate from infected cells. Lanes 5, 6 and 7 represent the corresponding control samples from un-infected cells. Lanes 4 and 8 are molecular weight markers. The bands (*) around 80 KDa are cellular proteins non-specifically recognized by the antibodies, while the bands (**) around 40 KDa are likely derived from a partially processed HA proteins as they are absent from un-infected cells. The HA2 bands appear at around 30 KDa.
Figure 4:
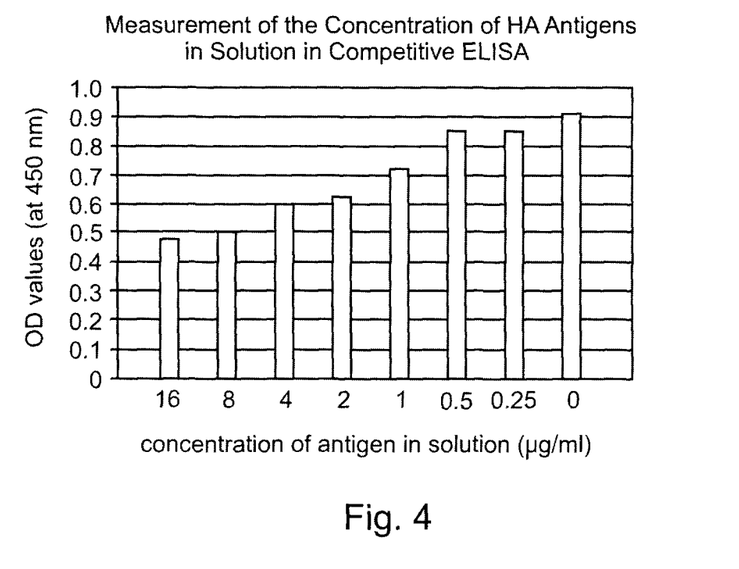
FIG. 4 depicts quantitative detection of HA proteins in solution using competitive ELISA. The antigens used were H5N1 HA antigens for both coating and competing antigens.
Figure 5:
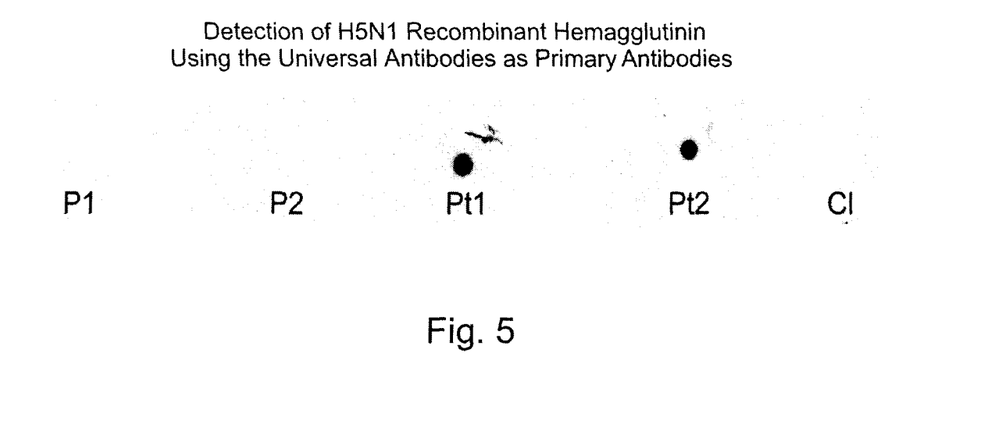

To determine the cross-reactivity of antibodies with other peptides (epitope mapping), the antibodies were pre-incubated with the other three peptides modified with Acp and KKC (Uni-2-Acp-KKC, Uni-3-Acp-KKC, Uni-4-Acp-KKC) and a modified control peptide (HA1-C-Acp-KKC) prior to the addition of the antibodies to the ELISA plate pre-coated with the Uni-1 peptide. As is shown in FIG. 2B, the three HA-derived peptides but not the control peptide can be nearly as effective in inhibiting the binding of the antibodies to Uni-1 as compared to the Uni-1 peptide itself. These data suggest that variations of amino acids in these peptides did not significantly affect the binding of the antibodies with the peptides representative of the minor substitutions in the fusion peptide region and that the antibodies did not bind to the spacer and the tripeptide KKC since all peptides including the unrelated control peptide contained both the 6-aminocaproic acid spacer and KKC.

Binding Specificities of the Antibodies to Diverse Strains of the Influenza Viruses Experiments were then designed to determine whether the antibodies could bind to diverse strains of influenza strains. To this end, 13 subtypes of influenza viruses available at our institutions were propagated in embryonated eggs. Allantoic fluid samples were used directly without any purification step so that the specificity of antibodies could be determined at the same time. As shown in FIG. 3A, the antibodies were found to bind all 13 subtypes. It is of note that the differences of reaction intensities amongst the subtypes were mostly likely due to the different titres of virus in the crude allantoic fluids since the binding intensities with anti-Uni-1 antibodies were largely consistent with that obtained with another anti-influenza proteins (NP). Moreover, the different nobilities of the HA proteins amongst the influenza subtypes are due to the differences of protein size or processing stages of the HA proteins. Importantly, the antibodies demonstrated remarkable specificity against the influenza HAs as no binding of the antibodies to proteins derived from allantoic fluids were detected. As expected, the antibodies could also detect HA proteins from influenza virus grown in embryonated eggs and purified for the preparation of human vaccines including influenza B (FIG. 3B).

The specificity of the antibodies was then determined in W.B. using samples derived from MDCK cells infected with influenza virus (PR-8). As shown in FIG. 3C, the antibodies were able to detect the HA2 fragments. Although cross-reaction of antibody to cellular protein was observed, the proteins detected by the antibodies were of higher molecular weight (around 80 KDa). The identity of the proteins with MW of approx. 40 KDa remains unclear but is likely to be intermediate species of the HA proteins since they were not present in the un-infected cells.

Quantitative Determination of the HA Proteins in Solution

To determine whether the antibodies could quantitatively bind diverse types of HA proteins in solution, a competitive ELISA was used. The H5N1 HA antigens (A/Vietname/1203/2004) were first treated with 8 M urea, and then used to coat ELISA plate (4 μg/mL in 4 M urea/PBS) at 4° C. overnight. The following day, the antibodies were incubated in 4 M urea/PBS with serially diluted antigens (H5N1 HA antigens) which had been pre-denatured with 8 M urea (see *Materials and Methods* above). Following incubation, the antigen-antibody mixture was then directly transferred to the ELISA plate coated with the antigens. FIG. 4 shows that the concentrations of the competing antigens in solution (HA recombinant proteins) were inversely proportional to the O.D. values.

Experiments were then designed to investigate whether the competitive ELISA could be adopted to quantitatively determine the concentration of different subtypes of HAs using H5N1 hemagglutinins as the standards (coating and competing antigens). To this end, H5 was coated in the plates. Serially diluted H5 was used as standard as described in FIG. 5. Different subtypes of recombinant HA proteins derived from influenza A (H1, H3, H5, H7 and H9) and influenza B were analyzed as samples with the expected values of 1.00 μg/mL (pre-determined by standard Bradford assay). The calculation is based on the currently accepted 4-parameter logistic model for immunoassay (Findley and Dillard 2007). As shown in Table 3, the quantities of other subtypes of HAs determined in the competitive ELISA were very close to the expected values predetermined by standard protein assays (Bradford protein assays). In addition, the concentration of H5 HA itself obtained using the universal antibodies were comparable to that with the H5 subtype specific antibodies. As expected, the H5 subtype specific antibodies failed to bind other subtypes of HA proteins. Similar data were obtained using H1N1 HA antigens as standard and competing antigens for the determination of different subtypes of HA antigens. Collectively, these data suggest that the antibodies raised using Uni-1-Acp-KKC-KLH conjugate are "universal" antibodies for the detection of HA proteins of all influenza viruses.

TABLE 3

Application of competitive ELISA to the detection of multiple subtypes of recombinant HA proteins with expected value of 1 μg/mL

| HA subtype | Uni-1 antibodies | H5 specific polyclonal antibody |
|---|---|---|
| H5* | 1.12 ± 0.08 | 1.26 ± 0.1 |
| H1 | 1.23 ± 0.12 | 0.00** |
| H3 | 1.29 ± 0.14 | 0.00 |
| H7 | 0.94 ± 0.21 | 0.00 |
| H9 | 1.23 ± 0.14 | 0.00 |
| B | 1.11 ± 0.09 | 0.00 |

*Recombinant H5N1 HA protein was used as both standards and also one of the samples for the determination of concentration in the same competitive ELISA.

**Values were out of the range (the same as the background), indicating the H5 subtype specific antibodies failed to bind HA proteins except itself.

Detection of Antigens Directly Absorbed on Nitrocellulose Filter

The antibodies were then assayed for their abilities to detect HA proteins directly absorbed on nitrocellulose filter without any denaturing step. As shown in FIG. 5, the antibodies could detect H5N1 HA proteins. Similar data were obtained for other subtypes of HA proteins.

Discussion Numerous attempts have been made in the past by various groups to generate antibodies against the most conserved regions in the HA proteins. The fusion peptide region has been identified to be the most conserved region among all subtypes of influenza A and B (Jackson et al. 1991; Gerhard et al. 2006). Although some antibodies can react the HA1-HA2 joint area (Horvath et al. 1998; Bianchi et al. 2005; Gerhard et al. 2005), there has been no report of antibodies that are specific against the more universally conserved fusion peptide region only. Generation of the antibodies against the conserved region is important because it enables health departments to be well ahead in pandemic flu preparedness. In the event of a pandemic situation, it is currently impossible to have quality control (Q.C.) reagents ready for the lot-release of a pandemic flu vaccine because preparation of the reagents would take at least several months and a pandemic flu could potentially spread globally in a few weeks. A universal assay system based on the present invention can alleviate this problem. A universal assay system based on the present invention could replace the current reagents for the annual (or seasonal) flu assay as well. Currently available prior art reference reagents for annual flu vaccine lot release (quantitation) are prepared annually and shipped globally by the National Institute for Biological Standards and Control (NIBSC) in the U.K. or the US FDA. There are often problems associated with the variability of the assay among different laboratories and reagents are also often in short supply and cannot meet global needs. By having a universal assay system, there will be no need to prepare and ship the reagents each year globally, thus substantially improving the Q.C. and simplifying the procedure for timely lot release of seasonal (annual) flu vaccines.

By using a bioinformatics approach, we confirmed that the fusion peptide region is conserved among all subtypes of influenza viruses with only minor substitutions. Specifically, four peptides most representative of the fusion peptide region were identified (Uni-1, Uni-2, Uni-3 and Uni-4). It is of note that all four peptides were very hydrophobic, making it extremely difficult to manipulate these peptides and its conjugates, i.e., solubilization, purification, conjugation or immunoassay. In addition, previous attempts using peptides or peptide-conjugates to generate against the fusion peptide have not been successful (Jackson et al. 19991; Horvath et al. 1998), suggesting this region is very weakly immunogenic. To overcome these hurdles, we first linked the identified peptide to a spacer, 6-aminocaproic acid to improve immunogenicity, followed by the addition of a tripeptide KKC to enable solubilization of the peptides and conjugation of the modified peptide to the carrier protein (KLH). Through these modifications, we were successful in generating specific antibodies against the fusion peptide. Although 6-aminocaproic acid as a spacer has been reported by others to link some haptens, e.g., dinitrophenyl, folic acid or polysaccharide, to carrier proteins (Scott et al, 1984; Das Sarma et al. 1995; Okawa et al. 1992), the use of the spacer has not been reported for influenza peptides. At this time, it remains unclear as to how the spacer would help the host in generating antibodies against the peptide although it is of note that two spacers might even be better than a single one for some haptens (Scott et al. 1984; Das Sarma et al. 1995; Okawa et al. 1992). We also engineered two spacers but the peptide conjugates turned out to be insoluble (jelly) in aqueous solution even with the addition of tripetide KKC.

The peptides modified and conjugated in our case were found to be sufficient in inducing antibodies against the immunogen (Uni-1-Acp-KKC-KLH). More importantly, it turned out these antibodies could bind equally well to other three peptide (Uni-2, Uni-3 and Uni-4), suggesting that the substitutions of amino acid exert little impact on the interaction of the antibodies with the viral sequences. Furthermore, we found the antibodies were able to bind various recombinant HA proteins (with similar minor substitutions of amino acids to that of the peptides) as well as 13 subtypes of influenza A with remarkable specificity as no cross-reactivity was observed using crude allantoic fluid preparations.

Thus, we here report the fusion peptide region among all influenza viruses are universally conserved across all sequences of influenza strains available in the public domain. However, amino acid sequences in the region do have some minor substitutions. We selected four peptides that are most representative of such variations. All of these peptides are highly hydrophobic. To overcome the weak immunogenicity and insolubility of the peptides, we linked the peptides to a 6-aminocaproic acid spacer, a tripeptide (KKC) and conjugated the modified peptide to KLH. The antibodies generated in rabbits demonstrated remarkable binding specificities for diverse strains of influenza A and B viruses in ELISA and W.B. It is also of note that the epitope (fusion peptide) in the whole HA protein could be exposed by 8 M urea treatment, and the antibody could still bind the antigens in 4 M urea. These conditions are important for the quantitative determination of the HA antigens in solution. Collectively, our data suggest that the antibodies described in this report are truly "universal" reagents for the detection of the HA proteins. Not only are they of practical application (vaccine potency testing in the event of a pandemic flu outbreak or as replacement for the current reagent for flu vaccine potency testing) but they are also valuable research tools in laboratory settings.

REFERENCES

The contents of the entirety of each of which are incorporated by this reference.

Bianchi E, et al. Universal influenza B vaccine based on the maturational cleavage site of the hemagglutinin precursor. *J. Virol.* (2005 June); 79(12):7380-8.

Bridges C B, et al. Effectiveness and cost-benefit of influenza vaccination of healthy working adults: A randomized controlled trial. *JAMA.* (2000 Oct. 4); 284(13):1655-63.

Carrat F and Flahault A. Influenza vaccine: the challenge of antigenic drift. *Vaccine.* (2007 Sep. 28); 25(39-40):6852-62.

Das Sarma J, et al. Antibody to folic acid: increased specificity and sensitivity in ELISA by using epsilon-aminocaproic acid modified BSA as the carrier protein. *J Immunol Methods.* (1995 Jul. 17); 184(1):1-6.

De Filette M, et al. Universal influenza A vaccine: optimization of M2-based constructs. *Virology.* (2005 Jun. 20); 337(1):149-61.

Epstein S L, et al. DNA vaccine expressing conserved influenza virus proteins protective against H5N1 challenge infection in mice. *Emerg Infect Dis.* (2002 August); 8(8):796-801.

Findlay J W and Dillard R F. Appropriate calibration curve fitting in ligand binding assays. *AAPS J.* (2007 Jun. 29); 9(2):E260-7.

Fouchier R A, et al. Characterization of a novel influenza A virus hemagglutinin subtype (H16) obtained from black-headed gulls. *J. Virol.* (2005 March); 79(5):2814-22.

Frace A M, et al. Modified M2 proteins produce heterotypic immunity against influenza A virus. *Vaccine.* (1999 May 4); 17(18):2237-44.

Fan J, Liang X, et al. Preclinical study of influenza virus A M2 peptide conjugate vaccines in mice, ferrets, and rhesus monkeys. *Vaccine*. (2004 Aug. 13); 22(23-24):2993-3003.

Gerhard W, et al. Prospects for universal influenza virus vaccine. *Emerg Infect Dis*. (2006 April); 12(4):569-74.

Gerhard W. Induction of influenza type A virus-specific resistance by immunization of mice with a synthetic multiple antigenic peptide vaccine that contains ectodomains of matrix protein 2. *Vaccine*. (2003 Jun. 2); 21(19-20):2616-26.

Horváth A, et al. A hemagglutinin-based multipeptide construct elicits enhanced protective immune response in mice against influenza A virus infection. *Immunol Lett*. (1998 February); 60(2-3):127-36.

Jackson D C and Brown L E. A synthetic peptide of influenza virus hemagglutinin as a model antigen and immunogen. *Pept Res*. (1991 May-June); 4(3):114-24.

Jackson D C, et al. The central role played by peptides in the immune response and the design of peptide-based vaccines against infectious diseases and cancer. *Curr Drug Targets*. (2002 April); 3(2):175-96.

Neirynck S, et al. A universal influenza A vaccine based on the extracellular domain of the M2 protein. *Nat Med*. (1999 October); 5(10):1157-63.

Nestorowicz A, et al. Antibodies elicited by influenza virus hemagglutinin fail to bind to synthetic peptides representing putative antigenic sites. *Mol Immunol*. (1985 February); 22(2):145-54.

Poland G A, et al. Influenza vaccines: a review and rationale for use in developed and underdeveloped countries. *Vaccine*. (2001 Mar. 21); 19(17-19):2216-20.

Röhm C, et al. Characterization of a novel influenza hemagglutinin, H15: criteria for determination of influenza A subtypes. *Virology*. (1996 Mar. 15); 217(2):508-16.

Schoofs P G, et al. Epitopes of an influenza viral peptide recognized by antibody at single amino acid resolution. *J. Immunol*. (1988 Jan. 15); 140(2):611-6.

Scott D, et al. Immunogenicity of biotinylated hapten-avidin complexes. *Mol Immunol*. (1984 November); 21(11):1055-60.

Simonsen L, et al. Mortality benefits of influenza vaccination in elderly people: an ongoing controversy. *Lancet Infect Dis*. (2007 October); 7(10):658-66.

Treanor J. Influenza vaccine—outmaneuvering antigenic shift and drift. *N Engl J. Med*. (2004 Jan. 15); 350(3):218-20.

Tomasini B R and Mosher D F. Conformational states of vitronectin: preferential expression of an antigenic epitope when vitronectin is covalently and noncovalently complexed with thrombin-antithrombin III or treated with urea. *Blood*. (1988 September); 72(3):903-12.

Wang K, et al. Expression and purification of an influenza hemagglutinin—one step closer to a recombinant protein-based influenza vaccine. *Vaccine*. (2006 Mar. 15); 24(12):2176-85.

World Health Organization. (1980). A revision of the system of nomenclature for influenza viruses: a W.H.O. memorandum. *Bull. W. H. O*. 58:585-591.

Wood J M, et al. The influence of the host cell on standardisation of influenza vaccine potency. *Dev Biol Stand*. (1999); 98:183-8; discussion 197.

Wu J, et al. Monoclonal antibody-mediated inhibition of HIV-1 reverse transcriptase polymerase activity. Interaction with a possible deoxynucleoside triphosphate binding domain. *J Biol Chem*. (1993 May 15); 268(14):9980-5.

Zambon M C. Epidemiology and pathogenesis of influenza. *J Antimicrob Chemother*. (1999 November); 44 Suppl B:3-9.

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

The invention claimed is:

1. An isolated antibody that binds specifically to a peptide consisting of the amino acid sequence as set forth in SEQ ID NO: 6.

2. The isolated antibody according to claim 1, wherein the antibody is an IgG.

3. A reagent for detecting influenza hemagglutinin, the reagent comprising the isolated antibody as defined in claim 1.

4. A method of detecting influenza hemagglutinin proteins in a target sample comprising: contacting an antibody as defined in claim 1 with the target sample; and, determining whether the antibody binds to the sample.

5. The method according to claim 4, further comprising determining concentration of the hemagglutinin proteins in the sample.

6. The method according to claim 5, wherein determining concentration comprises treating the sample with 8 M urea to expose hemagglutinin epitope to which the antibody binds, denaturing the antibody in 4 M urea, and conducting a competitive ELISA assay using the denatured antibody.

7. The method according to claim 4, wherein the hemagglutinin proteins are from influenza A or influenza B viruses.

8. The method according to claim 4, wherein the sample is a culture or an embryonated egg.

9. A method for determining potency of an influenza vaccine comprising: contacting an antibody as defined in claim 1 with a vaccine; and determining whether the antibody binds to hemagglutinin in the vaccine.

10. The method according to claim 9, further comprising determining concentration of the hemagglutinin protein in the vaccine.

11. A conjugate comprising: a conserved influenza virus peptide consisting of the amino acid sequence as set forth in SEQ ID NO: 6; a spacer molecule linked to the conserved influenza virus peptide; and a carrier protein linked to the spacer molecule.

12. The conjugate according to claim 11, wherein the spacer molecule comprises 6-aminocaproic acid.

13. The conjugate according to claim 11 or 12, wherein the carrier protein comprises keyhole limpet hemocyanin (KLH).

14. The conjugate according to claim 11 or 12, wherein the carrier protein is linked to the spacer molecule by KKC tripeptide.

15. A process for preparing an antibody that binds specifically to a conserved influenza virus peptide comprising the amino acid sequence as set forth in SEQ ID NO: 6 comprising inoculating a mammal with a conjugate as defined in claim 11 or 12 and recovering antibodies from the mammal.

16. The process according to claim 15, wherein the antibodies are purified in an affinity column using a ligand comprising a conserved influenza virus peptide comprising the amino acid sequence as set forth in SEQ ID NO: 6.

17. A modified peptide comprising: a conserved influenza virus peptide consisting of the amino acid sequence as set forth in SEQ ID NO: 6; and a spacer molecule linked to the conserved influenza virus peptide.

18. The modified peptide according to claim 17, further comprising KKC tripeptide linked to the spacer to facilitate dissolution of the modified peptide in aqueous solution.

19. The modified peptide according to claim 17 or 18, wherein the spacer molecule comprises 6-aminocaproic acid.

* * * * *

```
SEQUENCE LISTING

<160> NUMBER OF SEQ ID NOS: 6

<210> SEQ ID NO 1
<211> LENGTH: 14
<212> TYPE: PRT
<213> ORGANISM: Influenza A virus

<400> SEQUENCE: 1

Gly Leu Phe Gly Ala Ile Ala Gly Phe Ile Glu Gly Gly Trp
1               5                   10

<210> SEQ ID NO 2
<211> LENGTH: 14
<212> TYPE: PRT
<213> ORGANISM: Influenza A virus

<400> SEQUENCE: 2

Gly Ile Phe Gly Ala Ile Ala Gly Phe Ile Glu Gly Gly Trp
1               5                   10

<210> SEQ ID NO 3
<211> LENGTH: 14
<212> TYPE: PRT
<213> ORGANISM: Influenza A virus
```

```
-continued

<400> SEQUENCE: 3

Gly Leu Phe Gly Ala Ile Ala Gly Phe Ile Glu Gly Gly Trp
1               5                   10

<210> SEQ ID NO 4
<211> LENGTH: 14
<212> TYPE: PRT
<213> ORGANISM: Influenza A virus

<400> SEQUENCE: 4

Gly Ile Phe Gly Ala Ile Ala Gly Phe Ile Glu Asn Gly Trp
1               5                   10

<210> SEQ ID NO 5
<211> LENGTH: 13
<212> TYPE: PRT
<213> ORGANISM: Influenza A virus

<400> SEQUENCE: 5

Val Thr Gly Leu Arg Asn Ile Pro Ser Ile Gln Ser Arg
1               5                   10

<210> SEQ ID NO 6
<211> LENGTH: 14
<212> TYPE: PRT
<213> ORGANISM: Influenza A virus
<220> FEATURE:
<221> NAME/KEY: Xaa
<222> LOCATION: (2)..(2)
<223> OTHER INFORMATION: leu or ile
<220> FEATURE:
<221> NAME/KEY: Xaa
<222> LOCATION: (12)..(12)
<223> OTHER INFORMATION: gly or asn

<400> SEQUENCE: 6

Gly Xaa Phe Gly Ala Ile Ala Gly Phe Ile Glu Xaa Gly Trp
1               5                   10
```